United States Patent [19]

Andrews et al.

[11] Patent Number: 4,620,539
[45] Date of Patent: Nov. 4, 1986

[54] PISTOL GRIP, BONE DRILL

[76] Inventors: E. Trent Andrews, 2 Northgate Dr., San Francisco, Calif. 94127; Robert E. Moore, 4010 East Ave., Hayward, Calif. 94542

[21] Appl. No.: 512,175

[22] Filed: Jul. 11, 1983

[51] Int. Cl.4 .................... A61B 17/00; A61F 5/04
[52] U.S. Cl. .................... 128/303 R; 128/92 R; 128/92 VM; 128/92 V; 408/241 R; 279/1 K; 279/61
[58] Field of Search ............. 128/92 R, 92 E, 92 EB, 128/303 R; 408/241 R; 279/1 K, 60, 61

[56] References Cited

U.S. PATENT DOCUMENTS

| 1,308,798 | 7/1919 | Masland | 128/92 EB |
| 2,144,342 | 1/1939 | Morrison | 128/92 E |
| 2,243,718 | 5/1941 | Moreira | 128/92 E |
| 2,439,803 | 4/1948 | Giesen | 128/92 EB |
| 4,091,880 | 5/1978 | Troutner et al. | 128/92 EB |
| 4,317,578 | 3/1982 | Welch | 279/60 |
| 4,342,309 | 8/1982 | Eftehar | 128/92 EB |
| 4,389,146 | 6/1983 | Coder | 279/1 K |

Primary Examiner—Gene Mancene
Assistant Examiner—C. W. Shedd
Attorney, Agent, or Firm—Bielen and Peterson

[57] ABSTRACT

A pistol grip, bone drill with a lever lock for convenient locking of the drill chuck for manipulation of the chuck jaws, particularly for facilitating advances of the drill bit, the bone drill having a contoured pistol grip handle with a hand crank for rotating an elongated drill barrel by a conventional bevel gear mechanism, the drill barrel having an end chuck with a connected revolver cylinder having engagement holes for receiving a locking pin displaced by the lever lock.

10 Claims, 4 Drawing Figures

U.S. Patent   Nov. 4, 1986   4,620,539
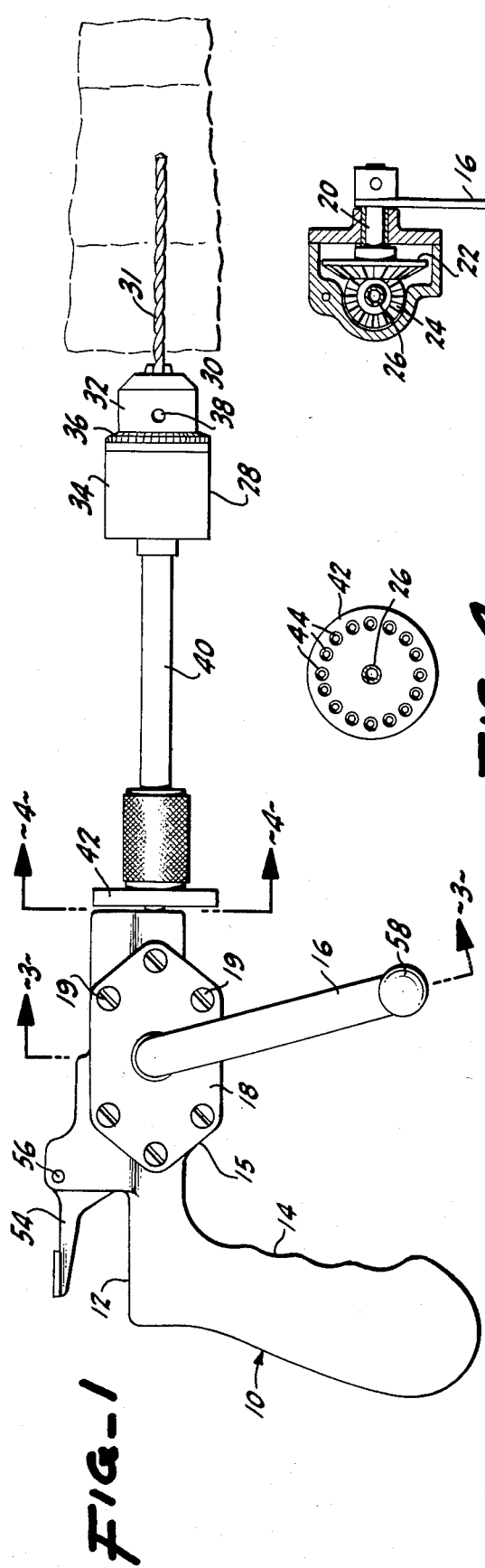
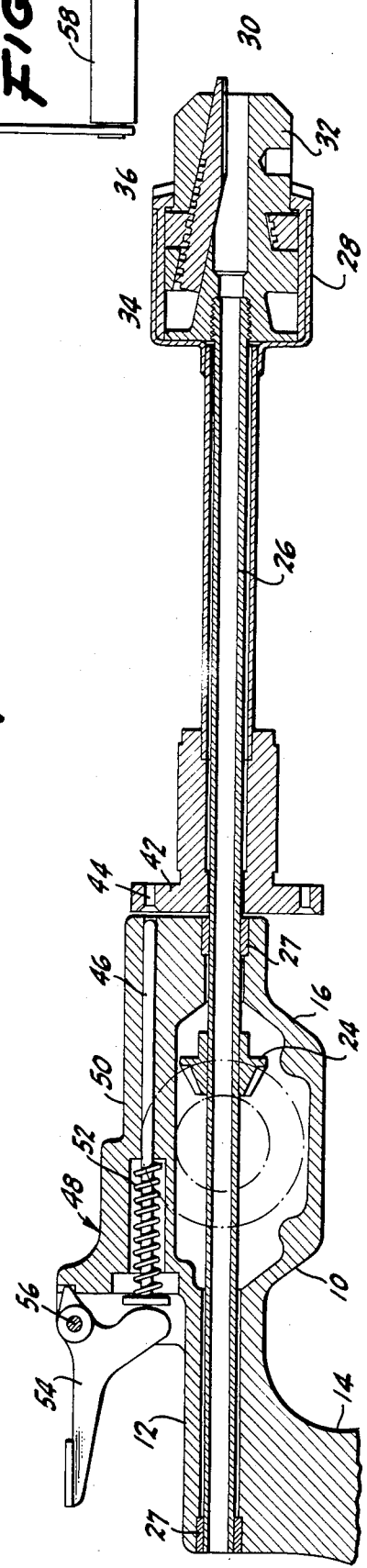

PISTOL GRIP, BONE DRILL

BACKGROUND OF THE INVENTION

This invention related to a mechanical hand drill devised for surgical use. The invented pistol grip, bone drill is used in operating procedures wherever conventional hand drills are used and is desired to facilitate procedures where a drill or K-wire must be advanced during the procedure. In many surgical procedures utilizing small diameter drills or pins, here generically terminal bits, it is desirable to extend only a short portion of the bit from the jaws of the chuck. This minimizes the chance for inadvertent breakage of the bit with the resultant problem of retrieval of a lodged broken bit from the patient. During the drilling operation, the chuck is repeatedly loosened and tightened to advance the drill until the desired depth is obtained. It is extremely important that the bit or adjacent components not become contaminated.

At critical moments, when the bit is to be advanced, dropping and contaminating the chuck key or repositioning the hands on the drill to loosen or tighten the chuck can result in risk to the patient. Because of the inward advance of the bit, contaminants can be transported deeply into the anatomy of a patient possibly causing complications.

Furthermore, since the concentration of the surgeon should focus on the accuracy of the bore, interruptions of concentrations should be minimized. The drill of this invention is designed to avoid such interruptions of concentration by eliminating the need for a key and allowing the surgeon to loosen, tighten or adjust the chuck without changing the position of his hands.

SUMMARY OF THE INVENTION

The bone drill of this invention is a pistol grip hand drill devised to assist the surgeon in accurately performing hand drilling procedures by providing a convenient mechanism for manipulating the chuck to permit loosening and tightening of the jaws of the chuck without repositioning of the hands.

The mechanism for manipulating the chuck comprises a lever lock that engages the chuck casing and holds it from rotation while the mandrel, geared to the hand crank, is allowed to turn, thereby causing displacement of the jaws according to the direction of hand crank rotation. The lever lock is located with respect to the pistol grip for convenient and comfortable operation by use of the user's thumb. No repositioning of the hands is required. Depressing the lever of the lever lock engages the chuck and restrains rotation of the chuck with repect to the mandrel.

Utilizing the lever lock during a drilling operation enables release and subsequent engagement of the jaws of the chuck on the bit to allow periodic advance of the bit as deemed expedient.

While a thumb activated lever lock was selected for the preferred embodiment, a finger activated trigger lock is deemed an operational equivalent.

BRIEF DESCRIPTION OF THE DRAWINGS

FIG. 1 is a side elevational view of the bone drill and drill bit.

FIG. 2 is an enlarged longitudinal cross sectional view of the bone drill of FIG. 1.

FIG. 3 is a cross sectional view taken on the line 3—3 in FIG. 1.

FIG. 4 is a cross sectional view taken on the lines 4—4 in FIG. 1.

DETAILED DESCRIPTION OF THE PREFERRED EMBODIMENT

Referring to FIGS. 1 and 2, the bone drill 10 of this invention is devised for surgical use, where it is desired to periodically extend the bit during the drilling procedure.

The bone drill has bitstock 12 with a comfortable pistol grip 14 that is joined to a gear casing 15 with a projecting hand crank 16 for comfortable and steady manual operation of the drill. The gear casing 15 has a cover plate 18 fastened to the casing 15 by a series of screws 19 through which the journal 20 of the hand crank 16 is installed. As shown in FIG. 3, the journal 20 is connected to a relatively large bevel gear 22 which meshes with a small bevel gear 24 at the middle of a hollow, elongated spindle 26. The spindle 26 is supported on bearings 27 and cooperates with a drill chuck to permit a K-wire or bit to extend from the chuck 28 through the hollow spindle 26 and out the end of the bitstock 12. The drill chuck 28 is in part conventional in construction with jaws 30 to grip a drill bit 31, a mandrel 32 connected to the spindle that contains the jaws and cams the jaws to an open or closed position, and, a chuck head 34 that rotates on the mandrel and advances or retracts the jaws on rotation by engagement of an inner threaded ring 35 on the chuck head 34 with the threaded jaws. The end rim of the chuck head 34 has a bevel gear 36 engageable by a conventional chuck key (not shown) insertable into a key hole 38 for operating the chuck in a customary manner. Uniquely, the chuck head is joined to an extension sleeve 40 that is connected to a locking cylinder 42. As shown in FIG. 4, the locking cylinder 42 includes a plurality of symmetrically spaced detent holes 44 into which a detent pin 46 of a locking mechanism 48 is selectively inserted to lock the cylinder 42 and hence the chuck head 34 from rotation. In this manner, with the chuck head 34 fixed, rotation of the spindle by the hand crank will cause displacement of the jaws.

The locking mechanism 48 has a pin housing 50 mounted on the top of the bitstock 12. The pin housing 50 retains the detent pin 46, and a return spring 52, and pivotally supports an actuating lever 54 on cross pin 56. The actuating lever 54 is conveniently situated for operation by the user's left thumb, while the user operates a crank knob 58 at the end of the hand crank 16 with his right hand.

The hollow drill spindle 26 is elongated to allow it to contain a long drill or K-wire with only a short section extending from the chuck. While the bit 31 must be repeatedly extended during a drilling operation, the accuracy and safety of the procedure outweighs the inconvenience.

The inconvenience is substantially reduced with the use of the locking mechanism. When it is desired to loosen the chuck to extract additional drill bit, the thumb hammer is depressed to advance the pin. With minor adjustment by the hand crank, the cylinder hole can be aligned with the pin to permit engagement of the pin into the hole. With the chuck head locked the hand crank can be used to force open the chuck jaws by rotation of the spindle with respect to the stationary head. The bit is generally lodged in the patient sufficiently to retain the bit while the drill is retracted, for repositioning on the bit. On repositioning, the crank is reversed, tightening the chuck jaws on the bit. The lever is released, and the pin is retracted by action of the spring to permit resumption of drilling. The process is repeated as necessary until the depth desired is obtained. If K-wire or a permanent pin bit is used, the chuck is finally loosened and withdrawn leaving the item in place.

While on the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A bone drill comprising:
   (a) a bitstock having a spindle and a drill chuck at the end of the spindle, said chuck having an outer chuck head and displaceable jaws housed in said chuck head for retaining a drill bit in said chuck, said bitstock having further a hand grip, and a hand crank with a geared connection to said spindle for rotating said spindle, and
   (b) a chuck lock mechanism having locking means engageable with said chuck for holding said chuck head to allow displacement of said jaws by use of said hand crank to rotate said spindle, said mechanism having an actuating means located on said bitstock proximate said hand grip for actuating said locking means with the user's hand grip hand without a substantial shift in the gripping position of either of the user's hands when actuating said mechanism and displacing said jaws from the gripping position of the hands used for rotating said spindle.

2. The bone drill of claim 1 wherein said spindle is hollow and has an elongated portion connected to said chuck to receive an elongated drill bit.

3. The bone drill of claim 2 wherein said chuck head has an extension portion on said elongated portion of said spindle engageable with 4. The bone drill of claim 3 wherein said extension portion includes a sleeve and a detent cylinder having a plurality of recesses, said chuck lock mechanism including a detent element selectively engageable in any one of said recesses.

5. The bone drill of claim 4 wherein said recesses comprise holes and said detent element comprises a pin insertable in said holes.

6. The bone drill of claim 5 wherein said actuating means comprising a thumb or finger operated actuator engageable with said pin.

7. The bone drill of claim 1 wherein said bitstock is constructed with a pistol grip.

8. The bone drill of claim 7 wherein said actuating means comprises a thumb operated lever pivotally mounted at the top of said bitstock.

9. The bone drill of claim 8 wherein said lever actuates a spring loaded detent pin engageable with said chuck head locking means.

10. The bone drill of claim 9 wherein said chuck head includes an extension cylinder having a concentric array of holes into any of which said pin is selectively insertable.

* * * * *